United States Patent
Humphrey

(10) Patent No.: US 6,579,898 B2
(45) Date of Patent: Jun. 17, 2003

(54) COMPOSITIONS HAVING IMPROVED BIOAVAILABILITY

(75) Inventor: Michael John Humphrey, Sandwich (GB)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 10/075,800

(22) Filed: Feb. 13, 2002

(65) Prior Publication Data

US 2002/0165120 A1 Nov. 7, 2002

Related U.S. Application Data

(60) Provisional application No. 60/277,400, filed on Mar. 20, 2001.

(30) Foreign Application Priority Data

Mar. 1, 2001 (GB) .............................................. 0105131

(51) Int. Cl.[7] ...................... A61P 25/06; A61K 31/404; A61K 38/00; A61K 31/275
(52) U.S. Cl. ........................................ 514/414; 514/415
(58) Field of Search .................................. 514/414, 415

(56) References Cited

U.S. PATENT DOCUMENTS

| 5,376,645 A | | 12/1994 | Stella et al. |
| 5,807,571 A | * | 9/1998 | List ............................. 424/449 |
| 6,004,927 A | | 12/1999 | Benet et al. |
| 6,060,499 A | * | 5/2000 | Plachetka .................... 514/415 |
| 6,110,940 A | | 8/2000 | Harding et al. |
| 6,166,025 A | * | 12/2000 | Harding et al. .......... 514/263.32 |
| 6,255,334 B1 | * | 7/2001 | Sands ........................... 514/414 |
| 6,376,550 B1 | * | 4/2002 | Raber et al. ................. 514/546 |
| 6,384,034 B2 | * | 5/2002 | Simitchieva et al. ... 514/252.01 |

FOREIGN PATENT DOCUMENTS

WO WO 9855148 12/1998

OTHER PUBLICATIONS

Stephens et al Brit. JL. Pharmacology 135(8):2038–2046 Resolution of P–Glycoprotein and Non–P–Glycoprotein Effects on Drug Permeability using Intestinal Tissues from MDRLA (−/−) MICG (Definitive Information . . . is scarce) 2002.*

Richard B. Kim, et al., The Drug Transporter P–alycoprotein Limits Oral Absorption and Brain Entry of HIV–1 Protease Inhibitors, Rapid Publication, J. Clin. Invest., vol. 101, No. 2, Jan. 1998, 289–294.

* cited by examiner

Primary Examiner—Shep K. Rose
(74) Attorney, Agent, or Firm—P. C. Richardson; P. H. Ginsburg; A. D. Joran

(57) ABSTRACT

A composition comprising eletriptan and a p-glycoprotein (p-gp) inhibitor useful for the treatment of migraine. The bioavailability of eletriptan can be increased by co-administering eletriptan with a p-gp inhibitor. The eletriptan and p-gp inhibitor can be administered together in a composition or as separate components. If administered separately, they can be embodied as a kit. Also provided is a method of treating migraine using said composition or sequential administration of components.

20 Claims, 1 Drawing Sheet

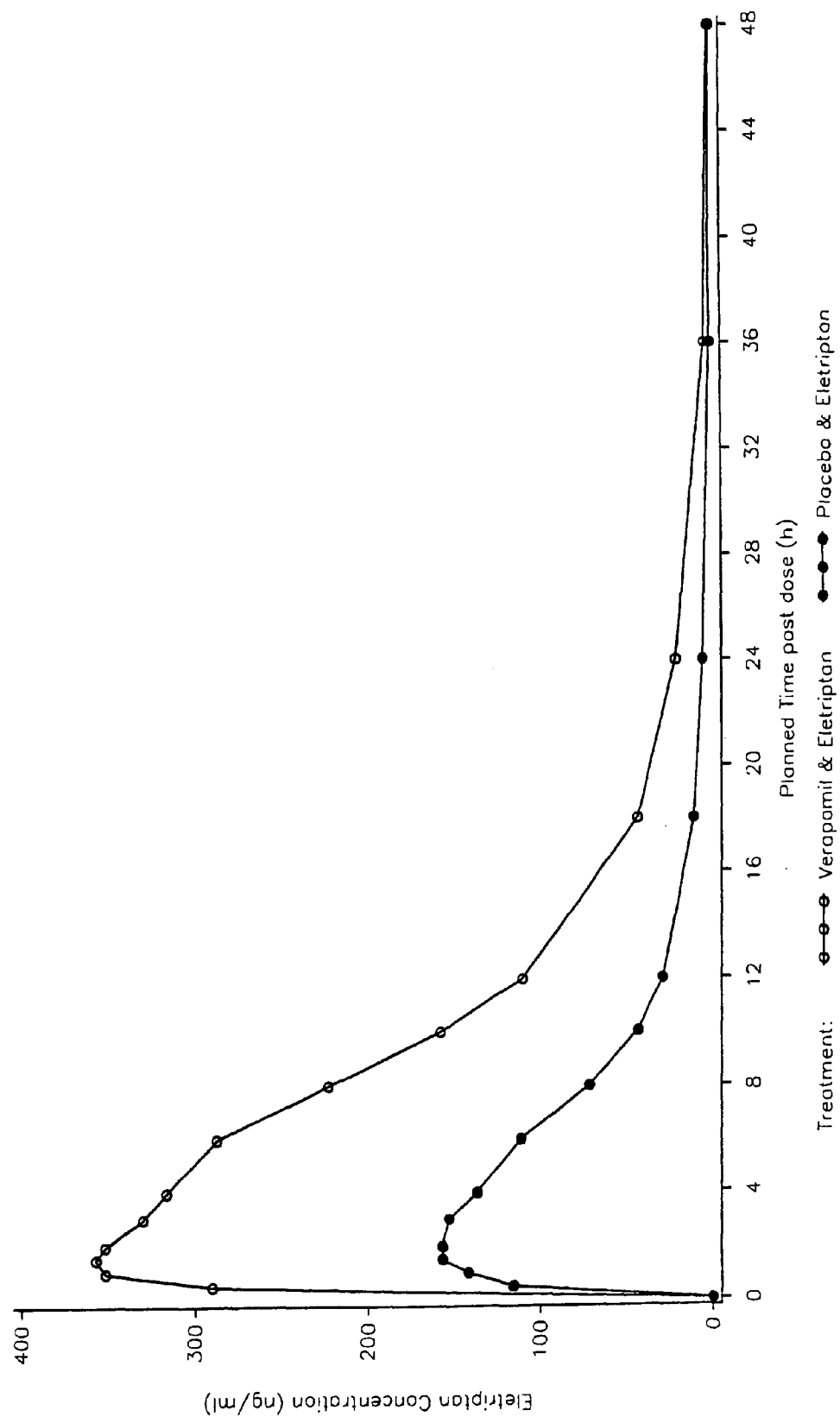

COMPOSITIONS HAVING IMPROVED BIOAVAILABILITY

The present application claims the benefit of U.S. Ser. No. 60/277,400, filed Mar. 20, 2001.

BACKGROUND OF THE INVENTION

The present invention relates to a method for increasing the oral bioavailability of eletriptan which comprises co-administering eletriptan with a p-glycoprotein (p-gp) inhibitor. The invention further relates to compositions and kits comprising eletriptan and a p-gp inhibitor.

Eletriptan is a potent and selective agonist for the vascular $5\text{-HT}_{1B}$ and neuronal $5\text{-HT}_{1D}$ receptors. Eletriptan causes selective constriction of intracranial vessels in the carotid distribution of animals, being more selective for the carotid distribution than for the coronary arteries. Although the precise cause and mechanism of migraine are not understood, a relationship between cranial blood vessels, which become dilated and inflamed in migraine, and the surrounding sensory nerves, is probably responsible. The resulting pain is thought to be an interaction between the distended blood vessels and the nerve fibres originating from the trigeminal ganglion. Eletriptan, a selective vasoconstrictor that is dosed orally, is therefore a convenient therapy for migraine.

Clinical trials using doses of 20, 40 and 80 mg show that the efficacy is increased and the time to abort a migraine attack is reduced with increasing dose level. Time to achieve effective plasma concentrations is reduced at the higher dose, while other factors, such as individual subject variability and environmental factors, are known to influence the rate and extent of exposure to eletriptan.

In vitro metabolism data indicate that eletriptan is predominantly metabolised by cytochrome P450-3A4 isozyme (CYP3A4). Therefore potent inhibition of this enzyme system by ketoconazole and erythromycin results in an increased systemic exposure and reduced clearance of eletriptan. The present invention is based, inter alia, on the results of a study to assess the safety, tolerability and pharmacokinetics of a single dose of eletriptan in the presence of a p-gp inhibitor, such as verapamil. Verapamil is a calcium ion influx inhibitor ('calcium channel blocker') having both systemic and coronary arteriodilator activity which is mainly used for the control of angina pectoris and hypertension.

Verapamil is known to be a moderate inhibitor of CYP3A4 metabolising enzyme ($K_i$=10 $\mu$M), which is the primary route of systemic clearance for eletriptan. However, in vitro human liver microsomal studies indicated no verapamil effect on eletriptan metabolism ($IC_{50}$>300 $\mu$M). Verapamil is known to alter hepatic blood flow, which could also influence eletriptan pharmacokinetics, so hepatic blood flow was also evaluated in the study. The study was designed to provide additional clinical information on the effect of a moderate CYP3A4 inhibitor on eletriptan pharmacokinetics and help define the in vitro/in vivo drug interaction correlation. The study was to be used to provide information on the potential for pharmacokinetic interactions between eletriptan and other CYP3A4 inhibitors.

Accordingly, it would be advantageous to have a formulation of eletriptan which increased the drug's oral bioavailability and thus could be dosed at lower doses and yet provide in a more consistent manner the efficacy benefits of a higher dose. An especially useful formulation could provide rapid onset and consistent action using a lower dose and reducing drug interactions and side-effects because of more consistent delivery. For example, a formulation which is, say, 50% more bioavailable could be dosed at 40 mg and provide the same systemic exposure as currently available formulations when dosed at 60 mg.

Certain excipients and drugs, when co-dosed with another drug, increase the oral absorption of that drug. Such excipients and drugs are thought to increase systemic exposure, at least in part, by inhibition of metabolism in the gut wall and liver and/or by inhibiting the p-gp/MDR efflux pumps found in the intestinal wall and other tissues. By way of further explanation, it is well known that a series of membrane proteins called Multi-Drug Resistance (MDR) proteins, which are heavily expressed in tumour cells, are able to excrete (or 'pump') certain anticarcinogenic drugs out of tumour cells. A portion of the resistance which tumours develop toward chemotherapy is believed to be due to the action of these proteins, which pump drugs out of tumour cells before the drugs have an opportunity to affect the cell. In general, it is believed that the drug passively partitions across the cell plasma membrane to get into the cell and is actively transported out of the cell by MDR proteins. MDR proteins are also known as P-glycoproteins (p-gps).

P-gps are also present in many types of normal cells, including, as indicated, those of the intestinal epithelium. Intestinal epithelial cells (IECs) are polarized cells which line the intestinal wall, providing a barrier between the gastrointestinal tract and the blood. The apical side of the IEC faces the intestinal lumen and the basolateral side faces the portal blood. Most drugs are absorbed passively, first crossing the IEC apical cell membrane and entering the IEC interior, then crossing the basolateral cell membrane, thus exiting the cell on the basolateral side, entering the extracellular space and ultimately partitioning into the portal bloodstream. P-gps are located on the apical cell membrane of the IEC and have the capacity to pump certain drugs out of the IEC back into the intestinal lumen. Thus IEC p-gps hinder the absorption of many drugs. The p-gps in IECs may also have a role in presenting drugs to the drug metabolising enzymes; it has been speculated that their purpose is to slow or prevent oral absorption of toxins. The p-gp efflux pump belongs to the superfamily of ATP-binding cassette (ABC) membrane transport proteins.

P-gps exhibit low substrate specificity and transport many kinds of molecules. The specificity is not rigorously understood and there is presently no way of predicting from drug molecular structure whether a specific drug will be a substrate for intestinal p-gps. Thus it is generally not possible to predict whether a particular drug or compound will be subject to the efflux pumping action discussed above. Also, if a particular drug has low oral bioavailability, it is generally not possible to predict (1) whether the low bioavailability is caused, wholly or partially, by the efflux pumps discussed above, nor (2) whether the low bioavailability can be increased by co-administration of a p-gp inhibitor. It is unknown in the art whether the rate and extent of bioavailability of eletriptan ($\log_e$ P0.5) can be improved by co-dosing eletriptan with another agent without also affecting systemic clearance.

European Patent Application No. 0742722 broadly claims, inter alia, a method for increasing the bioavailability of an orally administered hydrophobic pharmaceutical compound, for example, cyclosporine ($\log_e$ P3.0), which comprises orally administering said compound concurrently with a bioenhancer comprising an inhibitor of a cytochrome P450-3 A enzyme or an inhibitor of p-gp-mediated membrane transport.

We have now surprisingly found that administering eletriptan with a p-gp inhibitor increases the rate of onset of migraine abortion without altering systemic drug clearance. The higher and more consistent bioavailability of eletriptan is also expected to attenuate the potential effects of any drug interactions.

SUMMARY OF THE INVENTION

Thus the invention provides eletriptan in combination with a p-gp inhibitor for use as a medicament by means of which the rate and extent of oral bioavailability of eletriptan are significantly improved.

The invention further provides for the use of eletriptan in the preparation of a medicament combined with a p-gp inhibitor for the treatment of migraine and for the use of eletriptan in the preparation of a medicament for the treatment of migraine for administration to patients concomitantly receiving a p-gp inhibitor. Pharmaceutical compositions comprising eletriptan and a p-gp inhibitor and kits comprising separate compositions of each are also provided.

BRIEF DESCRIPTION OF THE DRAWING

FIG. 1 shows the mean plasma concentration of eletriptan at varying times after treatment, as described herein, with a combination of eletriptan with verapamil in comparison with the result after treatment with a combination of eletriptan with a placebo.

DETAILED DESCRIPTION OF THE INVENTION

Eletriptan can be employed in accord with this invention in the form of its pharmaceutically acceptable salts including hydrates thereof. All such forms are within the scope of the invention. The eletriptan employed is preferably the hydrobromide salt disclosed, for example, in European Patent No. 0776323. Reference to "eletriptan" in terms of therapeutic amounts is to the free base, i.e. the non-salt, non-hydrated molecule.

Use of the term 'p-gp inhibitor' shall be understood to include the types of compounds which are known in the art as MDR proteins or p-gp inhibitors. These may include both pharmaceutically-active compounds and compounds considered non-pharmaceutical in the sense that, but for their p-gp inhibitory activity, they are therapeutically inactive. The term 'p-gp inhibitor' shall be understood to mean that more than one p-gp inhibitor, separately or together in a composition, can be co-administered with eletriptan. For the purposes of the present description, the terms 'MDR protein' and 'p-gp inhibitor' are interchangeable and include the totality of IEC and brain endothelial cell membrane pump proteins which expel drugs from these cells.

In addition, it is noted that the affinity of eletriptan for the efflux pump protein(s) in the intestinal wall is unknown and that such affinity is generally unknown for other drugs which are inhibitors and/or are effluxed themselves. A p-gp inhibitor/MDR protein interaction which enhances eletriptan bioavailability may operate by one or more of a variety of mechanisms. That is, as is well known in the art, it may be a competitive inhibitor, a non-competitive inhibitor, an uncompetitive inhibitor, or operate by a mixed mechanism. Whether such an inhibitor can affect eletriptan efflux depends, inter alia, upon (1) the relative affinities of eletriptan and the inhibitor for p-gp/MDR, (2) the relative aqueous solubities of eletriptan and the inhibitor, because this will affect the concentration of the two at the pump in vivo when they are in competition, (3) the absolute aqueous solubility of the inhibitor, because it must achieve a sufficient concentration at the pump in vivo to effectively inhibit the pump, and (4) the dose of the inhibitor. For the purpose of this invention, a 'p-gp/MDR inhibitor' is any compound which improves the systemic exposure of eletriptan, when eletriptan is dosed by the buccal or oral route, and which is effluxed by and/or inhibits one or more of the drug efflux proteins of the intestinal epithelial cells. Evidence of efflux and/or inhibition may be obtained in an in vitro test such as a test of competition with, or inhibition of, eletriptan efflux in a cell culture model for intestinal epithelial cells. The Caco-2 cell model is one such model. According to the invention, this definition of a 'p-gp/MDR inhibitor' applies to any p-gp/MDR inhibitor, regardless of whether or not said p-gp/MDR inhibitor is a drug, that is, pharmaceutically active other than as a p-gp inhibitor.

Reference to "administration", "administering", "dosage" and "dosing" means oral administration. "Co-administration" of a combination of eletriptan and a p-gp inhibitor means that the two components can be administered together as a composition or as part of the same unitary dosage form. Co-administration also includes administering eletriptan and a p-gp inhibitor separately, but as part of the same therapeutic regimen. The two components, if administered separately, need not necessarily be administered at essentially the same time, although they can be if so desired. Thus co-administration includes, for example, administering eletriptan plus a p-gp inhibitor as separate dosages or dosage forms, but at the same time. Co-administration also includes separate administration at different times and in any order.

According to the present invention, eletriptan may be dosed at (1) the same level at which it would be dosed in the absence of a particular p-gp inhibitor if the goal is to increase the intracellular level of eletriptan; or (2) at a decreased level relative to the normal level at which it would be dosed in the absence of the p-gp inhibitor. The dose of eletriptan in the second case will usually be the normal dose proportionately decreased according to the increased bioavailability. For example, if the non-enhanced oral bioavailability of eletriptan is 50% and bioavailability in the presence of a p-gp inhibitor is 75%, then an 80 mg dose may be decreased to 80 mg×50/75=53.3 mg. The eletriptan may also be administered at an intermediate level between the two dosage values.

Eletriptan is presently administered orally as an acute treatment in a single dose of 20, 40, or 80 mg. When administered separately from a p-gp inhibitor, any oral dosage form of eletriptan, including suspensions, tablets, capsules and unit dose packets (referred to in the art as "sachets") may be employed, for example, as described in the latest *Physicians' Desk Reference.*

According to the present invention, eletriptan may, for example, be administered as a single dose with verapamil to abort a migraine attack; a second dose may be required if the migraine recurs within 24 hours. Those skilled in the art will appreciate that other eletriptan/p-gp inhibitor dose regimens are possible. Useful dose regimens are those which increase the bioavailability or brain penetration or other tissue levels of eletriptan. In a particularly preferred embodiment, eletriptan and a p-gp inhibitor are dosed at the same time, i.e. within 15 minutes of each other.

Oral bioavailability can be assessed by measuring AUC or $C_{max}$, both parameters well known in the art. AUC is a determination of the Area Under the Curve plotting the serum or plasma concentration of drug along the ordinate (Y-axis) against time along the abscissa (X-axis). Generally, the values for AUC represent a number of values taken from all the subjects in a patient test population and are therefore mean values averaged over the entire test population. $C_{max}$ is an abbreviation for the maximum drug concentration achieved in the serum or plasma of the test subject.

In a preferred embodiment of the invention, a p-gp inhibitor is co-administered with eletriptan in such an amount that the oral bioavailability of the eletriptan, as measured by AUC, is increased by at least 25%, that is, to an absolute bioavailability of at least 62.5%. In a more preferred embodiment, a p-gp inhibitor is co-administered in such an amount that the oral bioavailability of the eletriptan, as measured by AUC, is increased by at least 50%, that is, to an absolute bioavailability of at least 75%.

In a still more preferred embodiment, a p-gp inhibitor is co-administered in such an amount that the oral bioavailability of the eletriptan, as measured by AUC, is increased by at least 100%, that is, to an absolute bioavailability of 100%.

In another preferred embodiment of the invention, a p-gp inhibitor is co-administered with eletriptan in such an amount that the oral bioavailability of the eletriptan, as measured by $C_{max}$, is increased by at least 50%.

In a more preferred embodiment, a p-gp inhibitor is co-administered in such an amount that the oral bioavailability of the eletriptan, as measured by $C_{max}$, is increased by at least 100%. In a still more preferred embodiment, a p-gp inhibitor is co-administered in such an amount that the oral bioavailability of the eletriptan, as measured by $C_{max}$, is increased by at least 200%.

As indicated, the p-gp inhibitor may, in one aspect, be widely chosen from numerous compounds, including compounds which are non-pharmaceutical in the sense that they are not known to exhibit any therapeutic effect and/or which, but for their p-gp inhibitory activity, would be considered therapeutically inactive. In another aspect, the p-gp inhibitor may be selected from compounds which are themselves drugs and which, in addition to their known therapeutic function(s), also inhibit p-gp. Examples of p-gp inhibitors which are generally considered to be non-pharmaceutical and/or therapeutically inactive include those listed in Table I. These inhibitors may be dosed at doses of 25 mg to 3 g, preferably 50 mg to 2 g, more preferably 50 mg to 1 g.

TABLE I

Excipients and Non-pharmacological Agents which Increase the Bioavailability of Eletriptan

| Excipient/Agent |
| --- |
| PPO-PEO Block copolymers (Pluronics) |
| Cremophor-EL |
| d-alpha-tocopheryl-polyethyleneglycol-1000-succinate |
| Solutol-HS-15 |
| Polysorbate-80 |
| Oleic acid PEO esters |
| Stearic acid PEO esters |
| Triton-X100 |
| Nonidet P-40 |
| Benzoin gum |

In a preferred embodiment of the invention, the non-pharmaceutical p-gp inhibitor is selected from the class of polymers which are block copolymers of poly(propylene oxide) and poly(ethylene oxide). Examples of these block copolymers are available under the registered trademark Pluronic™ from BASF. Preferred polymers include Pluronic™ L43, L61, L62, L64, L81, L92, L101, P85, P103, P104 and P123, all available from BASF Corp., Parsippany, N.J. Of these, Pluronic™ L61, L62, L64, L81, L92, P85, P103 and P104 are particularly preferred. The compositions of these polymers can readily be obtained from BASF Corp.

In another preferred embodiment, the non-pharmaceutical p-gp inhibitor is a surfactant selected from the class of non-ionic surfactants. Examples are the PEO esters of oleic acid, preferably those wherein the PEO content is in the range 20–30 PEO units per molecule. Examples also include PEO esters of stearic acid, preferably those containing 10–35 PEO units per molecule. Useful surfactant p-gp inhibitors include polyoxyethylene ethers (e.g. Brij series), para-t-octylphenoxypolyoxyethylenes (e.g. Triton X-100), nonylphenoxypolyoxyethylenes (e.g. Igepal CO series), polyoxy-ethylene sorbitan esters (e.g. Tween series), ethoxylated fatty acids (e.g. Myrj series), polyoxyethyleneg-lycerides (e.g. Gelucire series, such as Gelucire 44/14) and sucrose fatty acid esters (e.g. Ryoto sugar ester series). Particularly preferred non-ionic surfactant p-gp inhibitors have a hydrophile-lipophile balance (HLB) number greater than about 13. Examples of p-gp inhibitors which are drugs having a therapeutic function other than p-gp inhibition include those listed in Table II:

TABLE II

Drugs and Drug Analogues which Increase the Bioavailability of Eletriptan

| Drug/Analogue | Drug/Analogue |
| --- | --- |
| Amiodarone | Aldosterone |
| Lidocaine | Clomiphene |
| Cefoperazone | Cortisol |
| Ceftriaxone | Dexamethasone |
| Erythromycin | Prednisone |
| Itraconazole | Progesterone |
| Chloroquine | Tamoxifen |
| Emetine | Desipramine |
| Quinidine | Trazodone |
| Hydroxychloroquine | Dipyridamole |
| Quinacrine | Reserpine |
| Quinine | Cyclosporin A |
| Bepridil | Colchicine |
| Diltiazem | FK-506 |
| Felodipine | Quercetin |
| Metaclopramide | SDZ PSC-833 |
| Nifedipine | SDZ 280-446 |
| Nisoldipine | Terfenadine |
| Nitrendipine | Tumor Necrosis Factor |
| Tiapamil | Vitamin A |
| Verapamil | Etoposide |
| Actinomycin D | R-Verapamil |
| Daunorubicin | Ketoconazole |
| Mitomycin-C | Tamoxifen |
| Taxol | RU-486 |
| Trimetrexase | Devapamil |
| Vinblastine | Gallopamil |
| Vincristine | Emopamil |
| Indinavir | L-Emopamil |
| Nelfinavir | R-Emopamil |
| Saquinavir | L-Verapamil |
| Ritonavir | Phenothiazines |
| Bupivacaine | |

The drugs listed in Table II may be administered in their conventional dosage amounts, for example, as given in the latest *Physicians' Desk Reference*.

In a preferred embodiment of the invention, the pharmaceutically-active p-gp inhibitor is an antimalarial drug such as chloroquine, hydroxychloroquine, quinidine, or quinine; an anti-AIDs drug such as nelfinavir, saquinavir, ritonavir, or indinavir; an antibiotic such as cefoperazone or ceftriaxone; an antifungal such as itraconazole; an immunosuppressant such as cyclosporine; or a calcium channel blocker such as verapamil. Verapamil is especially preferred.

As indicated, the invention further provides pharmaceutical compositions comprising eletriptan and a p-gp inhibitor. The components can be administered together, but will generally be administered in admixture with a suitable pharmaceutical excipient, diluent, or carrier selected with regard to the intended route of administration and standard pharmaceutical practice.

For example, eletriptan and a p-gp inhibitor can be administered orally, buccally, or sublingually in the form of tablets, capsules, multi-particulates, gels, films, ovules, elixirs, solutions, or suspensions, which may contain flavouring or colouring agents, for immediate-, delayed-, modified-, sustained-, pulsed- or controlled-release applications. Eletriptan and a p-gp inhibitor may also be administered as fast-dispersing or fast-dissolving dosage forms or in the form of a high energy dispersion or as coated particles. Suitable formulations of eletriptan and a p-gp inhibitor may be coated or uncoated.

Such solid pharmaceutical compositions, for example, tablets, may contain excipients such as microcrystalline cellulose, lactose, sodium citrate, calcium carbonate, dibasic calcium phosphate, glycine and starch (preferably corn, potato, or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

General Example

A formulation of the tablet could typically contain between about 0.1 mg and 200 mg of eletriptan and from 20 mg to 1000 mg of a p-gp inhibitor, whilst tablet fill weights may range from 50 mg to 1000 mg. An example of a formulation for a 20 mg tablet is illustrated below:

| Ingredient | % w/w |
| --- | --- |
| Eletriptan (free base or salt form) | 20.000 |
| Verapamil | 120.00 |
| Lactose | 64.125 |
| Starch | 1.375 |
| Croscarmellose sodium | 3.000 |
| Magnesium stearate | 1.500 |

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients include lactose, starch, a cellulose, milk sugar, or high molecular weight polyethylene glycols. For aqueous suspensions and/or elixirs, eletriptan and a p-gp inhibitor may be combined with various sweetening or flavouring agents, colouring matter or dyes, with emulsifying and/or suspending agents and with diluents such as water, ethanol, propylene glycol and glycerin, or combinations thereof.

Eletriptan and a p-gp inhibitor may also be administered parenterally, for example, intravenously, intra-arterially, intraperitoneally, intrathecally, intraventricularly, intraurethrally, intrasternally, intracranially, intramuscularly, or subcutaneously, or they may be administered by infusion or needleless injection techniques. For such parenteral administration, they are best used in the form of a sterile aqueous solution which may contain other substances, for example, enough salts or glucose to make the solution isotonic with blood. If necessary, the aqueous solutions may be suitably buffered, preferably to a pH of from 3 to 9. The preparation of suitable parenteral formulations under sterile conditions is readily accomplished by standard pharmaceutical techniques well known to those skilled in the art.

Thus tablets or capsules of eletriptan and a p-gp inhibitor may contain from 0.1 mg to 200 mg of eletriptan for administration singly or two or more at a time, as appropriate. The physician will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of the invention. The skilled person will appreciate that, in the treatment of certain conditions such as a migraine attack, eletriptan and a p-gp inhibitor may be taken as a single dose as and when needed.

Eletriptan and a p-gp inhibitor can also be administered intranasally or by inhalation and are conveniently delivered in the form of a dry powder inhaler or an aerosol spray presentation from a pressurised container, pump, spray, atomiser, or nebuliser, with or without the use of a suitable propellant, e.g. dichlorodifluoromethane, trichlorofluoromethane, dichlorotetrafluoroethane, a hydrofluoroalkane, such as 1,1,1,2-tetrafluoroethane (HFA 134A™) or 1,1,1,2,3,3,3-heptafluoropropane (HFA 227EA™), carbon dioxide, or other suitable gas. In the case of a pressurised aerosol, the dosage unit may be determined by providing a valve to deliver a metered amount. The pressurised container, pump, spray, atomiser, or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of eletriptan, a p-gp inhibitor and a suitable powder base such as lactose or starch.

Alternatively, eletriptan and a p-gp inhibitor can be administered in the form of a suppository or pessary, or they may be applied topically in the form of a gel, hydrogel, lotion, solution, cream, ointment, or dusting powder. Eletriptan and a p-gp inhibitor may also be administered dermally or transdermally, for example, by means of a skin patch. They may also be administered by the pulmonary or rectal routes.

Eletriptan and a p-gp inhibitor may also be administered by the ocular route. For ophthalmic use, they may be formulated as micronised suspensions in isotonic, pH-adjusted, sterile saline or, preferably, as solutions in isotonic, pH-adjusted, sterile saline, optionally in combination with a preservative such as a benzylalkonium chloride. Alternatively, they may be formulated in an ointment such as petrolatum.

For topical application to the skin, eletriptan and a p-gp inhibitor may be formulated as a suitable ointment containing eletriptan suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they may be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Eletriptan and a p-gp inhibitor may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability properties of a drug molecule. Drug-cyclodextrin complexes are generally useful for most dosage forms and administration routes. As an alternative to direct complexation with the drug, the cyclodextrin may be used as an auxiliary additive, e.g. as a carrier, diluent, or solubiliser. Alpha-, beta- and gamma-cyclodextrins are most commonly used and suitable examples are described in International Patent Application Nos. WO-A-91/11172, WO-A-94/02518 and WO-A-98/55148.

As indicated, the present invention also relates to treatment with a combination of eletriptan and a p-gp inhibitor which may be co-administered separately; the invention therefore also provides a kit comprising separate pharmaceutical compositions of each.

A kit according to the invention comprises (1) a therapeutically effective amount of a composition comprising eletriptan and a pharmaceutically acceptable carrier, diluent, or excipient in a first dosage form;

(2) a therapeutically effective amount of a composition comprising a compound which is a p-gp inhibitor and a pharmaceutically acceptable carrier, diluent, or excipient in a second dosage form; and (3) a container for containing said first and second dosage forms.

The relative amounts of (1) and (2) are such that, when co-administered separately, the bioavailability of eletriptan is increased. The kit comprises a container for containing the separate compositions, such as a divided bottle or a divided foil packet, wherein each compartment contains a plurality of dosage forms (e.g. tablets) comprising (1) or (2). Alternatively, rather than separating the active ingredient-containing dosage forms, the kit may contain separate compartments each of which contains a whole dosage itself comprising separate dosage forms. A typical example of a kit is a blister pack wherein each individual blister contains two (or more) tablets or capsules comprising one (or more) tablet(s) or capsule(s) of pharmaceutical composition (1) and one (or more) tablet(s) or capsule(s) of pharmaceutical composition (2).

The kit form is particularly advantageous when the separate components are preferably administered in different dosage forms (e.g. oral and parenteral), are administered at different dosage intervals, or when titration of the individual components of the combination is desirable.

EXAMPLES

The efficacy of a compound (drug, non-drug, or otherwise) as a p-gp inhibitor can be shown and approximated by a Caco-2 cell assay of the type described, for example, in Kim et al, J. Clin. Invest. 101, 289–294 (1998), and in Example 1. Caco-2 cells are colon carcinoma cells which are considered in the art to be a reasonable model for the intestinal epithelium.

While the ability of a compound to inhibit p-gp/MDR-mediated eletriptan efflux may be determined by the Caco-2 cell assay, improved eletriptan bioavailability is best shown by human clinical studies of the type described in Example 2.

Example 1

Eletriptan Transport Across Human Intestinal (Caco-2) Cell Monolayers

Caco-2 cell monolayers were grown on permeable 24 well filter supports (1 $\mu$m poresize) and used at Day 15–28. The permeability of eletriptan was examined in both the apical and basolateral direction (absorptive) and basolateral to apical (secretory) direction at different concentrations and in the presence of p-gp inhibitors.

In studies examining the effect of concentration, 1, 10, 25 and 100 $\mu$M solutions of eletriptan in HBSS were added to the donor chamber and Hank's balanced salt solution (HBSS) was added to the acceptor chamber. The volume of the apical and basolateral chambers were 0.25 ml and 1 ml respectively. The wells were incubated for 2 hours at 37° C. with orbital shaking. After the incubation period, samples were removed from both chambers and analysed by LC-MS. Permeability ($P_{app}$) values were determined using standard equations described in the literature (Arturrson et al, 1990).

Where the p-gp inhibitors verapamil, ketoconazole and erythromycin were included, they were added to both the donor and acceptor chambers at concentrations of 100, 50 and 100 $\mu$M respectively. In these studies, a concentration of 10 $\mu$M eletriptan was used. Appropriate controls containing no inhibitor were included.

An impermeable marker, $^{14}$C mannitol, was included in all studies to ensure the monolayers were intact. Monolayers exhibiting mannitol flux of >1×10$^{-6}$cm/sec $P_{app}$ were disregarded from the study.

The results are given in the following tables:

| | Absorptive A -> B $P_{app} \times 10^{-6}$ (cm/s) | Std. Dev. | Secretory B -> A $P_{app} \times 10^{-6}$ (cm/s) | Std. Dev. |
|---|---|---|---|---|
| Concentration of eletriptan ($\mu$M) | | | | |
| 1 | 17.0 | 1 | 41.8 | 2.6 |
| 10 | 20.2 | 0.2 | 36.1 | 4.2 |
| 25 | 21.1 | 0.4 | 34.1 | 3 |
| 100 | 29.9 | 0.5 | 32.8 | 1.6 |
| P-gp inhibitor | | | | |
| Control (no inhibitor) | 16.0 | 1.4 | 32.6 | 1.2 |
| 0.2 mM Verapamil | 24.5 | 0.3 | 24.5 | 2.0 |
| 50 $\mu$M ketoconazole | 24.3 | 0.4 | 19.8 | 2.8 |

These data demonstrate that eletriptan is a substrate for the p-gp efflux transporter. Eletriptan exhibits a higher secretory flux (basolateral-to-apical; B→A) than absorptive flux (apical-to-basolateral; A→B) at low concentrations which is consistent with p-gp-mediated efflux. Larger absorptive $P_{app}$ values are found at higher concentrations due to saturation of the p-gp.

Conclusion: Transport of eletriptan in the presence of p-gp inhibitors is significantly increased in the absorptive direction and decreased in the secretory direction.

Example 2

Effect of Verapamil on the Pharmacokinetics of Eletriptan

This was an open randomized, placebo-controlled, two-period crossover study to investigate the effects of sustained-release verapamil on the pharmacokinetics, safety and toleration of a single 80 mg oral dose of eletriptan.

Healthy male and female subjects aged 18 to 45 years inclusive with weight 60–100 kg for males and 50–80 kg for females received 120 mg verapamil twice daily on Days 1 and 2 rising to 240 mg twice daily on Days 3 to 6, followed by a 240 mg dose on the morning of Day 7. A single 80 mg dose of eletriptan was administered on the morning of Day 6. Placebo was given twice daily on Days 1 and 6 and once on the morning of day 7. Twice daily doses were taken 12 hours apart.

Plasma eletriptan concentrations were assayed up to 48 hours post-eletriptan on Day 6. Concentrations were determined by specific reversed phase high performance liquid chromatography (hplc) with ultraviolet detection with a calibration range of 0.5 to 250 ng/ml.

$Log_e$-transformed AUC and $C_{max}$ and untransformed $T_{max}$ and $k_{el}$ for eletriptan following verapamil were compared against eletriptan following placebo. The ratios between anti-logged treatment means and the corresponding anti-logged Cls for AUC and $C_{max}$ were also measured.

Conclusions: As shown in FIG. 1, eletriptan mean AUC increased 2.7-fold and mean $C_{max}$ increased 2.2-fold in the presence of verapamil. There was evidence that the $T_{max}$ was reduced in the presence of verapamil. The mean terminal elimination rate constant ($k_{el}$) was reduced very slightly in the presence of verapamil. The overall coefficients of variation for both AUC and $C_{max}$ were similar for eletriptan either in the presence or absence of verapamil.

Similar results in respect of increased AUC and $C_{max}$ were obtained with ketoconazole and erythromycin, but in both cases $k_{el}$ was significantly reduced.

Example 3

Effect of Vitamin E-TPGS on the Pharmacokinetics of Eletriptan

This was a crossover study to assess the effects of Vitamin E-TGPS on the rate of absorption of eletriptan. Four male beagle dogs were orally dosed in the fasted state with a 20 ml aqueous formulation comprising (a) 0.2 mg/kg eletriptan;
(b) 0.2 mg/kg eletriptan coformulated with 6.67 mg/kg of Vitamin E-TGPS;
(c) 1.0 mg/kg eletriptan; and
(d) 1.0 mg/kg eletriptan coformulated with 6.67 mg/kg of Vitamin E-TGPS.

Blood samples (2.5 ml) were collected at 0, 0.17, 0.33, 0.5, 1, 2, 4, 6, 8, 12 and 24 hours after dosing and centrifuged. The resulting plasma samples were deep frozen until analysed for eletriptan by hplc with electrochemical detection. Rapid attainment and high peak concentrations of eletriptan were observed with $T_{max}$ values in the range 1.0 and 1.7 hours and $C_{max}$ values in the range 7 to 15 ng/ml.

What is claimed is:

1. A method of treating migraine in a subject comprising administering to said subject an amount of a composition comprising eletriptan in combination with a p-gp inhibitor effective to treat migraine in said subject selected from the group consisting of amiodarone, aldosterone, lidocaine, clomiphene, cefoperazone, cortisol, ceftriaxone, dexamethasone, erythromycin, prednisone, itraconazole, progesterone, chloroquine, tamoxifen, emetine, desipramine, quinidine, trazodone, hydroxychloroquine, dipyridamole, quinacrine, reserpine, quinine, cyclosporin A, bepridil, colchicine, diltiazem, FK-506, felodipine, quercetin, SDZ PSC-833, nifedipine, SDZ 280-446, nisoldipine, terfenadine, nitrendipine, tumor necrosis factor, tiapamil, vitamin A, verapamil, etoposide, actinomycin D, r-verapamil, daunorubicin, ketoconazole, mitomycin-C, tamoxifen, taxol, RU-486, trimetrexase, devapamil, vinblastine, gallopamil, vincristine, emopamil, indinavir, 1-emopamil, nelfinavir, r-emopamil, saquinavir, 1-verapamil, ritonavir, phenothiazines, bupivacaine, or administering in sequence to said subject eletriptan and the selected p-gp inhibitor, each in an amount effective to treat migraine in said subject.

2. The method of treating migraine according to claim 1 wherein said composition provides an increase in oral bioavailability of eletriptan, as measured by AUC, of at least 25% relative to dosing in absence of p-gp inhibitor.

3. The method of treating migraine according to claim 1 wherein said composition provides an increase in oral bioavailability of eletriptan, as measured by AUC, of at least 50% relative to dosing in absence of p-gp inhibitor.

4. The method of treating migraine according to claim 1 wherein said composition provides an increase in oral bioavailability of eletriptan, as measured by AUC, of 100% relative to dosing in absence of p-gp inhibitor.

5. The method of treating migraine according to claim 1 wherein said composition provides an increase in oral bioavailability of eletriptan, as measured by $C_{max}$, of at least 50% relative to dosing in absence of p-gp inhibitor.

6. The method of treating migraine according to claim 1 wherein said composition provides an increase in oral bioavailability of eletriptan, as measured by $C_{max}$, of at least 100% relative to dosing in absence of p-gp inhibitor.

7. The method of treating migraine according to claim 1 wherein said composition provides an increase in oral bioavailability of eletriptan, as measured by $C_{max}$, of at least 200% relative to dosing in absence of p-gp inhibitor.

8. The method of treating migraine according to claim 3 wherein said increase is measured in blood serum.

9. The method of treating migraine according to claim 3 wherein said composition provides an oral bioavailability for eletriptan, as measured by AUC, of greater than 50%.

10. The method of treating migraine according to claim 3 wherein said composition improves rate of onset of migraine abortion by at least 25% relative to dosing in absence of p-gp inhibitor.

11. A pharmaceutical composition comprising eletriptan, a p-gp inhibitor selected from the group consisting of amiodarone, aldosterone, lidocaine, clomiphene, cefoperazone, cortisol, ceftriaxone, dexamethasone, erythromycin, prednisone, itraconazole, progesterone, chloroquine, tamoxifen, emetine, desipramine, quinidine, trazodone, hydroxychloroquine, dipyridamole, quinacrine, reserpine, quinine, cyclosporin A, bepridil, colchicine, diltiazem, FK-506, felodipine, quercetin, SDZ PSC-833, nifedipine, SDZ 280-446, nisoldipine, terfenadine, nitrendipine, tumor necrosis factor, tiapamil, vitamin A, verapamil, etoposide, actinomycin D, r-verapamil, daunorubicin, ketoconazole, mitomycin-C, tamoxifen, taxol, RU-486, trimetrexase, devapamil, vinblastine, gallopamil, vincristine, emopamil, indinavir, 1-emopamil, nelfinavir, r-emopamil, saquinavir, 1-verapamil, ritonavir, phenothiazines, bupivacaine, and a pharmaceutically acceptable carrier, diluent, or excipient.

12. The composition according to claim 11 wherein oral bioavailability of eletriptan, as measured by AUC, is increased by at least 25% relative to dosing in absence of p-gp inhibitor.

13. The composition according to claim 11 wherein oral bioavailablility of eletriptan, as measured by AUC, is increased by at least 50% relative to dosing in absence of p-gp inhibitor.

14. The composition according to claim 11 wherein oral bioavailability of eletriptan, as measured by AUC, is increased by 100% relative to dosing in absence of p-gp inhibitor.

15. The composition according to claim 11 wherein oral bioavailability of eletriptan, as measured by $C_{max}$, is increased by at least 50% relative to dosing in absence of p-gp inhibitor.

16. The composition according to claim 11 wherein oral bioavailablility of eletriptan, as measured by $C_{max}$, is increased by at least 100% relative to dosing in absence of p-gp inhibitor.

17. The composition according to claim 11 wherein oral bioavailability of eletriptan, as measured by $C_{max}$, is increased by at least 200% relative to dosing in absence of p-gp inhibitor.

18. The composition according to claim 12 wherein said increase is measured in blood serum.

19. The composition according to claim 11 which improves rate of onset of migraine abortion by at least 25% relative to dosing in absence of p-gp inhibitor.

20. A kit comprising (1) a therapeutically effective amount of a composition comprising eletriptan and a pharmaceutically acceptable carrier, diluent, or excipient, in a first dosage form;

(2) a therapeutically effective amount of a composition comprising a compound which is a p-gp inhibitor and a pharmaceutically acceptable carrier, diluent, or excipient, in a second dosage form; and (3) a container for containing said first and second dosage forms.

* * * * *